United States Patent [19]

Morgans, Jr. et al.

[11] Patent Number: 5,225,590

[45] Date of Patent: Jul. 6, 1993

[54] ALKOXY METHYL ETHER AND ALKOXY METHYL ESTER DERIVATIVES

[75] Inventors: David J. Morgans, Jr.; Harlan H. Chapman, both of Palo Alto, Calif.

[73] Assignee: Syntex (U.S.A.) Inc., Palo Alto, Calif.

[21] Appl. No.: 186,503

[22] Filed: Apr. 26, 1988

Related U.S. Application Data

[60] Division of Ser. No. 853,278, Apr. 17, 1986, abandoned, which is a continuation-in-part of Ser. No. 795,381, Nov. 12, 1985, abandoned, which is a continuation-in-part of Ser. No. 681,037, Dec. 12, 1984, abandoned.

[51] Int. Cl.$^5$ .............................................. C07C 67/02
[52] U.S. Cl. .................................. 560/234; 560/117; 560/240
[58] Field of Search ................. 560/234, 240, 117

[56] References Cited

PUBLICATIONS

Migrdichian, Organic Synthesis, vol. 1, Reinhold Publishing Corp., N.Y., 1951, pp. 79 and 202.
Hughes et al, Journal of the American Chemical Society vol. 76, Oct. 20, 1954, p. 5161.
Weygand et al, Preparative Organic Chemistry John Wiley & Sons, N.Y., 1972, pp. 393–394.

*Primary Examiner*—Arthur C. Prescott
*Attorney, Agent, or Firm*—James J. Wong; David A. Lowin; Tom M. Moran

[57] ABSTRACT

Intermediates and methods for producing intermediates for use in preparing 9-(1,3-dihydroxy-2-propoxymethyl)-guanine and esters and ethers thereof.

17 Claims, No Drawings

ALKOXY METHYL ETHER AND ALKOXY METHYL ESTER DERIVATIVES

BACKGROUND OF THE INVENTION

This is a division of U.S. Ser. No. 853,278, filed Apr. 17, 1986, now abandoned; which is a continuation-in-part of U.S. Ser. No. 795,381, filed Nov. 12, 1985, now abandoned; which is a continuation in part of U.S. Ser. No. 681,037, filed Dec. 12, 1984, now abandoned; which disclosures are incorporated herein by reference.

FIELD OF THE INVENTION

This invention relates to alkoxymethyl ethers and alkoxymethyl esters of glycerols and to methods for producing alkoxymethyl ethers and alkoxymethyl esters of glycerols. In particular this invention relates to intermediates and methods for producing intermediates for the production of 9-(1,3-dihydroxy-2-propoxymethyl) guanine and its esters and ethers.

9-(1,3-dihydroxy-2-propoxymethyl) guanine (hereinafter DHPG) and its esters are potent antiviral agents and have been prepared by methods disclosed in U.S. Pat. No. 4,355,032 and European Patent Applications 49,072; 72,027 and 74,306. Similar compounds having similar side chains are disclosed in U.S. Pat. Nos. 4,347,360 and 4,199,574. The present invention relates to new intermediates and to an improved process whereby the new DHPG ether or ester side chain intermediate is prepared in fewer steps than other currently used processes and produces fewer undesirable by-products.

The side chain intermediates for the preparation of DHPG and its ethers and esters have been produced in the past by reacting epichlorohydrin with a benzyl alcohol, to obtain a symmetrically substituted 1,3-dibenzyl glycerol, which is then chloronethylated. The chloromethyl compound is converted to the acetate or formate ester, which is then reacted with guanine to add to the 9 position of guanine. See U.S. Pat. No. 4,355,032.

An alternate synthesis is disclosed in U.S. Pat. No. 4,347,360 where 1,3-dichloro-2 propanol is reacted with sodium benzylate forming the chloromethoxy derivative which is reacted further with a purine base.

A third method is disclosed in European Patent Application 74,306 published Mar. 3, 1983. In this application the side chain is made by starting with glycerol formal, a mixture of 1,3-dioxan-5-ol and 1,3-dioxolane-4-methanol. The glycerol formal is acylated and the mixture is separated. The acylated compound is then reacted with acetic anhydride in the presence of $ZnCl_2$ to give a compound that can be reacted with a purine. These three syntheses are all multistep methods that involve complicated separation and purification techniques and do not involve the intermediates of this invention.

It would be advantageous to have a process that was straight forward (required fewer steps), used easily obtainable starting materials, did not create unwanted isomers, and allowed facile substitution of the terminal esters. The claimed invention provides all these features. In particular, DHPG and a wide variety of 1,3-di-esters and 1,3-di-ethers of DHPG can easily be made using the intermediates and process of this invention.

SUMMARY OF THE INVENTION

This invention provides a process for preparing a compound represented by the Formula $$R^4-\overset{O}{\underset{\|}{C}}-O\frown O\begin{bmatrix}O-R^1\\O-R^3\end{bmatrix} \qquad \text{Formula A}$$

wherein $R^1$ and $R^3$ are selected from the group consisting of hydrogen, optionally substituted lower alkyl, acyl, 1-adamantanoyl, optionally substituted phenyl and optionally substituted phenyl lower alkyl and $R^4$ is optionally substituted lower alkyl, comprising:

reacting a compound represented by the Formula $$(R^4-\overset{O}{\underset{\|}{C}}-)_2O \qquad \text{Formula B}$$

wherein each $R^4$ is independently selected from the group as defined above, with a compound represented by the Formula $$R^6O\frown O\begin{bmatrix}O-R^1\\O-R^3\end{bmatrix} \qquad \text{Formula C'}$$

wherein $R^1$ and $R^3$ are as previously defined, and $R^6$ is defined as optionally substituted lower alkyl, in the presence of a catalytic amount of a Lewis acid for time sufficient to form a compound represented by Formula A.

This invention further provides a process for preparing the compound of the Formula:

$$R^7-O\begin{bmatrix}O-R^1\\O-R^3\end{bmatrix} \qquad \text{Formula C}$$

wherein $R^1$ and $R^3$ are selected from the group consisting of hydrogen, optionally substituted lower alkyl, acyl, 1-adamantanoyl, optionally substituted phenyl and optionally substituted phenyl lower alkyl and $R^7$ is defined as $R^4C(O)OCH_2$ or $R^6OCH_2$ wherein $R^4$ and $R^6$ are defined as optionally substituted lower alkyl by reacting a compound of Formula D:

$$R^4-\overset{O}{\underset{\|}{C}}-O\frown OR^6 \qquad \text{Formula D}$$

wherein $R^4$ and $R^6$ are as previously defined with a compound of Formula E:

$$R^1-O\diagdown\diagup O-R^3 \\ | \\ OH \qquad \text{Formula E}$$

wherein $R^1$ and $R^3$ are as previously defined, in the presence of a protic acid.

This invention further provides a method for making compounds represented by the Formula:

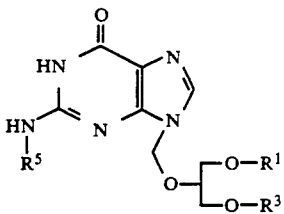

wherein $R^1$ and $R^3$ are selected from the group consisting of hydrogen, optionally substituted lower alkyl, acyl, 1-adamantanoyl, optionally substituted phenyl and optionally substituted phenyl lower alkyl and $R^5$ is acyl or hydrogen, comprising:

(a) reacting optionally substituted guanine with a compound represented by the Formula:

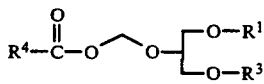

Formula A wherein $R^1$ and $R^3$ are selected from the group consisting of hydrogen, optionally substituted lower alkyl, acyl, 1-adamantanoyl, optionally substituted phenyl and optionally substituted phenyl lower alkyl and $R^4$ is optionally substituted lower alkyl, optionally followed by (b) treating the resulting mixture with a lower alkyl alcohol.

Furthermore this invention provides a class of compounds useful as intermediates in the process of this invention represented by the Formula:

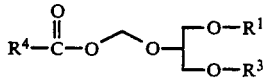

Formula A wherein $R^1$ and $R^3$ are selected from the group consisting of hydrogen, optionally substituted lower alkyl, 1-adamantanoyl, acyl, optionally substituted, optionally substituted phenyl and optionally substituted phenyl lower alkyl and $R^4$ is defined as optionally substituted lower alkyl.

Furthermore this invention provides a class of compounds useful as intermediates in the process of this invention represented by the Formula:

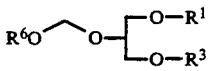

Formula C' wherein $R^1$ and $R^3$ are selected from the group consisting of hydrogen, optionally substituted lower alkyl, acyl, 1-adamantanoyl, optionally substituted phenyl and optionally substituted phenyl lower alkyl and $R^6$ is defined as optionally substituted lower alkyl.

DETAILED DESCRIPTION OF THE INVENTION

As used in the specification and appended claims, unless specified to the contrary, the following terms have the meaning indicated.

"Lower alkyl" is defined as any straight or branched chain hydrocarbon group having 1 to 4 carbon atoms, for example, methyl, ethyl, propyl, i-propyl, butyl, t-butyl, and the like.

"Optionally substituted" refers to a substitution on an alkyl or phenyl group with halogen atoms, lower alkyl groups, and phenyl groups.

"Optionally substituted guanine" refers to a guanine molecule which is optionally substituted with acyl and/or (alkyl)$_3$Si groups on the amino group at position 2 and on the nitrogen at position 9.

"Acyl" is defined herein as optionally substituted alkyl-C(O) having four to twenty carbon atoms in the alkyl chain 1-adamantyl-(C=O), i.e., 1-adamantoyl, optionally substituted phenyl-C(O), or optionally substituted alkyl phenyl-C(O) where the optional substitution is on the phenyl ring. Examples include n-hexanoyl, n-heptanoyl, palmitoyl, steracanoyl, arachidoyl, pivaloyl, 1-methyl-1-cyclohexane-carboxoyl, 2-octyl-decanoyl, benzoyl, p-chlorobenzoyl, toluoyl, phenylacetyl, 3-phenylpropanoyl, and 4-phenylbutanoyl.

"Pivalic acid" is 2,2-dimethyl propionic acid.

"1-adamantanoyl" refers the radical having the structure identified below.

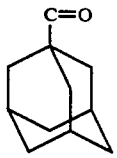

Phenyl refers to a six-member carbon ring which contains 3 double bonds.

Alkyl phenyl refers to a phenyl group which has an alkyl chain substituted on it wherein alkyl is as defined above.

"Hydrogen donor" refers to any substance that can serve as a source of active hydrogen. Some examples of hydrogen donors are hydrogen gas, cyclohexane, 1,4-cyclohexadiene and the like. In some cases catalysts may be used in conjunction with hydrogen donors, for example, the noble metals, for example, platinum, palladium, and rhodium may be used as a finely divided metal or as metal supported on any conventional catalyst support, for example, carbon, alumina, or silica.

"Acid" when used in this specification will normally be modified by either a specific named acid, for example, pivalic acid, or would be modified as a protic acid or a Lewis acid.

"Lewis acid" refers to any acid that does not have an abstractable proton. Examples include Be(CH$_3$)$_2$, BF$_3$, B(O-alkyl)$_3$, Al(CH$_3$), Al(Cl)$_3$, Fe$^{3+}$, Mg$^{2+}$, Ca$^{2+}$, Cu$^+$, TiCl$_4$, Hg$^{2+}$, Co$^{2+}$, Fe$^{2+}$, Zn$^{2+}$, and the like. A comprehensive list of Lewis acids can be found at *Chem. Rev.*, 75, 1, (1975), on page 2.

"Protic acid" refers to any Bronsted acid having a pK$_a$ less than 2.0, and preferably less than 1.0 that has an abstractable proton. Examples include mineral acids, for example, nitric acid, sulfuric acid, phosphoric acid, hydrogen halides, for example, hydrochloric acid; organic acids, for example, trifloroacetic acid, organic sulfonic acids, for example phenyl sulfonic acid, and particularly preferred, para-toluene sulfonic acid; and acidic resins, for example Amberlyst ® (Rohm and Haas).

"Protecting groups" refer to any group which can protect the functionality of a compound and may be removed by hydrolysis or hydrogenation. Examples of protecting groups useful in the present invention are sterically hindered groups (where sterically hindered refers to a particular atomic grouping which hinders or inhibits an expected chemical reaction due to its bulk), benzyl or optionally substituted benzyl, or alkyl groups, and sterically hindered silyl groups of the general formula $R_3Si(R_2)$—.

"Alkoxy methyl ether" means a compound represented by the formula $$A-O-CH_2-O-B$$

where A and B are optionally substituted lower alkyl groups.

One process of the present invention as depicted in Reaction Scheme I.

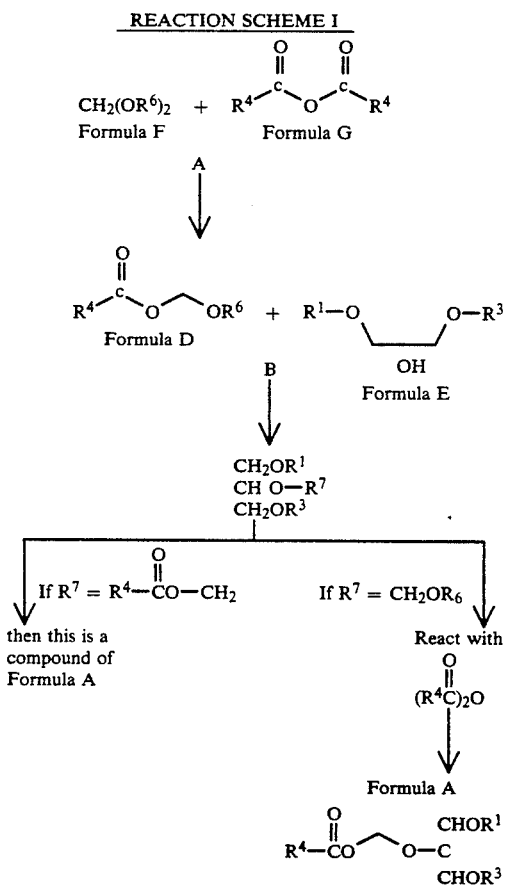

wherein $R^1$ and $R^3$ are selected from the group consisting of hydrogen, optionally substituted lower alkyl, 1-adamantanoyl, acyl, optionally substituted phenyl and optionally substituted phenyl lower alkyl, and $R^7$ is $R^4C(O)OCH_2$ or $R^6OCH_2$ wherein $R^4$ and $R^6$ are independently selected from optionally substituted lower alkyl.

In Reaction Sequence A a dialkyloxy methane Formula F is reacted with an anhydride Formula G in the presence of a protic acid catalyst. The two reactants are present in about a one to one molar ratio in the presence of a catalytic amount of a protic acid, for example, organic sulfonic acids, for example, para-toluene sulfonic acid, or catalytic amounts of a mineral acid, for example, hydrochloric acid or sulfuric acid. The reaction can be done in an aprotic hydrocarbon solvent, for example benzene, or neat, typically at reflux temperature of the solution. The solution is reacted for 1 to 12 hours, 6 hours being about typical. See the method of *J. Am. Cem. Soc.*, 76, page 5161 (1954).

It is preferred that the anhydride and dialkyloxy methane be symmetrical because the number of possible products is dramatically reduced by using symmetical reagents. Asymmetrical anhydrides or asymmetrical alkyloxy methanes can, of course, be reacted together in the process of this invention. In certain cases asymmetrical anhydrides can be selective for one of the possible products.

The 1,3-dialkanoyl glycerol Formula E can be prepared in one of two ways. Treatment of glycerol with slightly more than two equivalents of an acid chloride or an acid anhydride in aprotic solvents in the presence of organic base, for example, trialkylamines, and a nucleophilic catalyst, for example, pyridine can afford the 1,3-dialkanoyl glycerol Formula E.

Alternatively these compounds are accessible from dihydroxyacetone using the method of *J. Org. Chem.*, 35, 2082, (1970). Treatment of dihydroxyacetone in pyridine with an equivalent of the appropriate fatty acid chloride followed by reduction of the central keto group with borohydride in tetrahydrofuran can afford the 1,3-dialkanoyl glycerol Formula E.

In Reaction Sequence B compound Formula D and compound Formula E are reacted together in the presence of a protic acid catalyst, for example, organic sulfonic acids, for example, para-toluene sulfonic acid, or catalytic amounts of a mineral acid, for example, hydrochloric acid or sufuric acid, to produce a mixture (Formula C). This mixture is composed of compound of Formula A and compound of Formula C'. Compounds of Formula D and Formula E are mixed together neat with a catalytic amount of a protic acid catalyst. It is preferable that an excess of the compound of Formula D be used, the excess being useful as a solvent for the reaction. The reactants can be mixed together without the necessity of an external heat source, although the application of heat will speed the reaction. Reaction B can be exothermic, and when the temperature drops to ambient temperature the reaction is over. The reaction takes between 1 and 6 hours, typically about 2 hours to complete.

The mixture (Formula C) will vary depending on the starting materials. For example, if $R^1$ and $R^3$ are benzyl, reaction sequence B produces mostly Formula A, but if $R^1$ and $R^3$ are pivaloyl reaction sequence B produces mostly Formula C'. Reaction sequence C may be deleted if the product of Reaction Sequence B is a compound of Formula A. Otherwise, the compounds are reacted according to Reaction Sequence C.

In Reaction Sequence C, the mixture of compounds of Formula C is then further reacted in presence of a alkyl anhydride and a Lewis acid catalyst. It is preferred that the anhydride used in this reaction be a symmetrical anhydride to reduce the possible number of products formed, although this is not a requirement for this reaction.

The catalytic acid is preferably a non-protic Lewis acid catalyst, for example, boron trifluoride, or aluminum trichloride. The reaction temperature climbs from ambient temperature to about 50° C. at which point temperature control is applied. The temperature of the reaction is generally kept between about 45° and 65° C., preferably between about 50° C. and about 60° C.

The progress of the reaction is typically followed by thin layer chromatography (TLC) to indicate the amount of reaction that has occurred. After between 60 and 180 minutes the reaction will normally be complete. The reaction mixture is extracted with an organic solvent which is washed with sodium carbonate and water. The organic layer is then dried and the product Formula A obtained by the evaporation of the solvent.

Once compound Formula A is obtained esters or ethers of DHPG or DHPG itself can then be easily obtained, if desired. Reaction Schemes II and III show this process.

REACTION SCHEME II

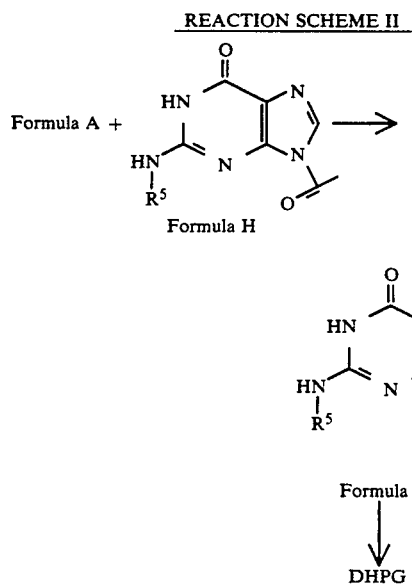

Compound Formula A can be converted into a 2-haloalkyl-1,3-diacyl glycerol using HX where X is a fluorine, chlorine, bromine or iodine atom, in methylene chloride.

Protected guanine Formula H produced for example by the methods of Tshido et al., *Bull. Chem. Soc. Japan*, 37, 1389 (1964), is reacted with compound Formula A, as isolated from Reaction Scheme I. $R^5$ is acyl or hydrogen and, if acyl, together with the guanine's nitrogen that $R^5$ protects, forms, preferably, a monoamide of a lower alkanoic acid, for example, acetamide, or propionamide. The reaction is conducted at elevated temperature under vacuum, in the presence of an acidic catalyst, for example para-toluene sulfonic acid. The DHPG derivative, Formula J, is then formed, where $R^1$ and $R^3$ are as previously defined. If the derivative ester or ether is directly useful, for example dipivaloyl DHPG or di-adamantanoyl DHPG, then no further reactions are necessary if $R^5$ was hydrogen. If $R^5$ was acyl, then the ester or ether of DHPG can be prepared by reacting compound of Formula J with, for example, methanolic ammonia. If DHPG is desired, Formula J can be deprotected (removal of $R^1$, $R^3$, and $R^5$), forming DHPG, by reacting the compound with the mixture of, for example, ammonium hydroxide and water.

REACTION SCHEME III

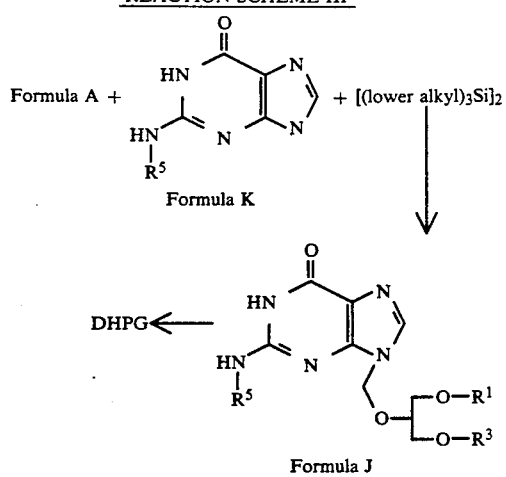

Alternatively, Formula A can be reacted directly with a trialkylsilyl protected guanine to afford the DHPG ester or ether. Guanine or an optionally substituted guanine derivative is heated in an aprotic hydrocarbon solvent, for example, toluene, or xylenes and the like, with greater than 3 molar equivalents of hexa-lower-alkyl-silazane, for example, hexamethylsilazane, hexaethylsilazane and the like, and a catalyst. The catalyst is selected from the group of trialkyl silyl sulfates, chlorosilanes, ammonium sulfate and pyridine. A volume of volatiles equal to the volume of hydrocarbon solvent is removed by vacuum distillation from the resulting solution. Then compound Formula A is added and the mixture is heated at a temperature greater than ambient temperature until anaylsis of the mixture by TLC shows the consumption of Formula A and the formation of the DHPG ester or ether (Formula J). Treatment of the reaction mixture at this time to remove all the trimethylsilyl groups, for example, by heating with lower alkyl alcohols, for example, methanol, ethanol or isopropanol, affords the DHPG ester or ether which can be purified by standard methods. If $R^5$ is acyl, then $R^5$ can be removed with, for example, methanolic ammonia to obtain the DHPG ester or ether. If DHPG is desired, Formula J can be deprotected ($R^1$, $R^3$, and $R^5$) by reaction with a mixture of, for example, ammonium hydroxide and water.

EXAMPLES

The following nonlimiting examples show various aspects of this invention.

EXAMPLE 1

1,3-di(1-adamantanoyl) glycerol

In a flask under nitrogen 1.053 gms of glycerol is dissolved in 4 ml of pyridine and 6 ml of methylene chloride and cooled to about −10° C. Then 5.00 gms of (1-adamantanoyl)-chloride (Aldrich Chemical Co.) is added in one portion and stirring is continued for about half an hour with cooling and then another two hours at ambient temperature. The resulting solid is filtered and washed with methylene chloride. The combined organic layers are washed twice with dilute aqueous HCl and then once with water and dried over magnesium sulfate. 1,3-di(1-adamantanoyl) glycerol is isolated as an oil.

Proton NMR, CDCl$_3$ 1.5-2.2(m, 30H); 2.3-2.7(br. s, 1H); 4.1-4.3(m, 5H).

Using a similar method but substituting the appropriate compound for (1-adamantanoyl)chloride, the following compounds were prepared:
1,3-di-benzoyl glycerol;
1,3-di-pivaloyl glycerol;
1,3-di-butanoyl glycerol;
1,3-di-s-butanoyl glycerol;
1,3-di-t-butanoyl glycerol;
1,3-di-propanoyl glycerol;
1,3-di-hexanoyl glycerol;
1,3-di-heptanoyl glycerol;
1,3-di-octanoyl glycerol;
1,3-di-nonanoyl glycerol;
1,3-di-decanoyl glycerol;
1,3-di-undecanoyl glycerol;
1,3-di-dodecanoyl glycerol;
1,3-di-tridecanoyl glycerol;
1,3-di-tetradecanoyl glycerol;
1,3-di-pentadecanoyl glycerol;
1,3-di-hexadecanoyl glycerol;
1,3-di-heptadecanoyl glycerol;
1,3-di-octadecanoyl glycerol;
1,3-di-nonadecanoyl glycerol;
1,3-di-eicosanoyl glycerol;
1,3-di-p-chlorobenzoyl glycerol;
1,3-di-o-chlorobenzoyl glycerol;
1,3-di-m-chlorobenzoyl glycerol;
1,3-di-p-bromobenzoyl glycerol;
1,3-di-o-bromobenzoyl glycerol;
1,3-di-m-bromobenzoyl glycerol;
1,3-di-p-fluorobenzoyl glycerol;
1,3-di-o-fluorobenzoyl glycerol;
1,3-di-m-fluorobenzoyl glycerol;
1,3-di-p-iodobenzoyl glycerol;
1,3-di-o-iodobenzoyl glycerol;
1,3-di-m-iodobenzoyl glycerol;
1,3-di-toluoyl glycerol;
1,3-di-phenylacetyl glycerol;
1,3-di-3-phenylpropanoyl glycerol;
1,3-di-4-phenylbutanoyl glycerol.

The 1,3-di-alkyl glycerols can be prepared according to the method described in U.S. Pat. No. 4,355,032.

EXAMPLE 2

1,3-di-isopropyl-2-propanoyloxymethyl glycerol 154 g of 1,3-di-isopropyl glycerol and 616 ml of methoxymethylpropionate plus 9.98 g para-toluene sulfonic acid were mixed in a 2-liter round bottom flask equipped with magnetic stirring and an internal thermometer. A 6° temperature rise occurred over 10 minutes. This was followed by a steady drop in temperature back to ambient temperature. A TLC (25% ethyl acetate / 75% hexane rf=0.69, silica) check after 45 minutes of reaction showed a nearly complete consumption of the starting alcohol.

The reaction mixture was added to a separatory funnel with 500 ml of hexane as an organic phase followed by washing the organic layer with 500 ml of water and washing it twice with 500 ml of saturated aqueous sodium bicarbonate and a final 500 ml wash of water. The organic layer was then dried over anhydrous magnesium sulfate and stripped on a rotary evaporator and 1,3-di-isopropyl-2-propanoyloxymethyl glycerol isolated.

Proton NMR, CDCl$_3$, 1.1(complex, 9H); 2.3(q, 2H); 3.4-4.0(complex, 7H); 5.2(s, 2H).

Similarly, substituting the appropriate compound of Example 1, the following compounds were prepared:
1,3-di-methyl-2-propanoyloxymethyl glycerol;
1,3-di-ethyl-2-propanoyloxymethyl glycerol;
1,3-di-propyl-2-propanoyloxymethyl glycerol;
1,3-di-butyl-2-propanoyloxymethyl glycerol;
1,3-di-s-butyl-2-propanoyloxymethyl glycerol;
1,3-di-t-butyl-2-propanoyloxymethyl glycerol;
1,3-di-phenyl-2-propanoyloxymethyl glycerol;
1,3-di-benzyl-2-propanoyloxymethyl glycerol.

In a similar manner, methoxymethylbutanoate, or methoxymethylpentanoate can be used to prepare the appropriate 1,3-di-alkyl-2-alkanoyloxymethyl glycerol.

EXAMPLE 3

1,3-dipropanoyl-2-propanoyloxymethyl glycerol 339 g of propionic anhydride and 185 g of the crude oil produced from the reaction of Example 2 (1,3-di-isopropyl-2-propanoyloxymethyl glycerol) and were added to a 2-liter, 3-neck, round bottom flask equipped with a magnetic stirrer, a reflux condenser, an internal thermometer and a nitrogen inlet set up so that heating or cooling could be applied rapidly. 17.9 g of borontrifluoride etherate was then added in one portion. The reaction temperature immediately climbed from about 20° C. (ambient) to about 50° C. at which point cooling was applied. The reaction temperature was carefully kept between 50° C. and 60° C. by heating or cooling as necessary. Reaction progress was followed by TLC (25% ethyl acetate/75% hexane rf=0.31, silica) of the reaction mixture.

After 100 minutes the reaction mixture was added to a separatory funnel with 500 ml of toluene. The organic layer was washed with 500 ml of saturated aqueous sodium carbonate and twice with 500 ml of water. The organic layer was then dried over anhydrous sodium sulfate filtered and stripped on a rotary evaporator under a 26 inches of mercury vacuum. A crude black oil was recovered and then purified by 2 passes through a wiped film distillation apparatus. The purified oil was 1,3-dipropanoyl-2-propanoyloxymethyl glycerol.

Proton NMR, CDCl$_3$, 1.1(t, 9H); 2.3(q, 6H); 4.1(complex, 5H); 5.2(s, 2H).

In a similar manner the appropriate 1,3-di-alkyl-2-propanoyloxymethyl glycerols of Example 2 can be reacted to prepare 1,3-di-propanoyl2-propanoyloxymethyl glycerol.

In a similar manner the appropriate 1,3-di-alkyl-2-acetyloxymethyl glycerol, 1,3-di-alkyl-2-butanoyloxymethyl glycerol, or 1,3-di-alkyl-2-pentanoyloxymethyl glycerol can be reacted to form the corresponding 1,3-di-acyl compound.

EXAMPLE 4

1,3-dibenzyl-2-acetoxymethyl glycerol 75 g di-benzyl glycerol, 5.25 g paratoluene sulfonic acid, 300 ml hexane, and 300 ml methoxymethyl acetate were added to a 2-l round bottom flask with magnetic stirring, internal thermometer and drying tube. The reaction mixture was brought to 60°-65° C. for 90 minutes, followed by TLC (20% ethyl acetate/80% hexane rf=0.31, silica) followed by cooling, transferring to a separatory funnel, washing once with 700 ml H$_2$O, and once with 700 ml saturated aqueous sodium carbonate solution. 150 ml CH$_2$Cl$_2$ was then added followed by a final wash with 700 ml H₂O. The organic layer was dried over sodium sulfate, filtered, and stripped at high vacuum to give 1,3-dibenzyl-2-acetoxymethyl glycerol as a clear oil.

Proton NMR, CDCl₃ 1.9(s, 3H); 3.6(complex, 4H); 4.0(m, 1H); 4.5(s, 4H); 5.2(s, 2H); 7.2(complex, 10H).

Similarly, using the appropriate 1,3-di-substituted glycerol from Example 1, the following compounds were prepared:
1,3-di-methyl-2-acetoxymethyl glycerol;
1,3-di-ethyl-2-acetoxymethyl glycerol;
1,3-di-propyl-2-acetoxymethyl glycerol;
1,3-di-isopropyl-2-acetoxymethyl glycerol;
1,3-di-butyl-2-acetoxymethyl glycerol;
1,3-di-s-butyl-2-acetoxymethyl glycerol;
1,3-di-t-butyl-2-acetoxymethyl glycerol;
1,3-di-phenyl-2-acetoxymethyl glycerol.

EXAMPLE 5

1,3-dipivaloyl-2-methoxymethyl glycerol 50.45 g of 1,3-dipivaloyl glycerol was dissolved in 200 ml of methoxymethyl acetate. After the addition of 2.5 g of p-toluenesulfonic acid monohydrate, the mixture was stirred for 1 hr then diluted with 200 ml of hexane and washed twice with 200 ml saturated aqueous sodium carbonate, once with aqueous NaCl solutions, dried over anhydrous magnesium sulfate and concentrated in vacuo to afford 1,3-dipivaloyl-2-methoxymethyl glycerol as a colorless oil.

Proton NMR, CDCl₃, 1.2(s, 18H); 3.4(s, 3H); 4.1(m, 1H); 4.2(m, 4H); 4.7(s, 2H).

Similarly using the appropriate 1,3-di-substituted glycerols from Example 1, the following compounds were prepared:
1,3-di(1-adamantanoyl)-2-methoxymethyl glycerol Proton NMR, CDCl₃, 1.6–2.1(complex, 30H); 3.4(s, 3H); 4.1(complex, 1H); 4.2(complex, 4H); 4.8(s, 2H).
1,3-di-benzoyl-2-methoxymethyl glycerol;
1,3-di-pivaloyl-2-methoxymethyl glycerol;
1,3-di-butanoyl-2-methoxymethyl glycerol;
1,3-di-s-butanoyl-2-methoxymethyl glycerol;
1,3-di-t-butanoyl-2-methoxymethyl glycerol;
1,3-di-propanoyl-2-methoxymethyl glycerol;
1,3-di-hexanoyl-2-methoxymethyl glycerol;
1,3-di-heptanoyl-2-methoxymethyl glycerol;
1,3-di-octanoyl-2-methoxymethyl glycerol;
1,3-di-nonanoyl-2-methoxymethyl glycerol;
1,3-di-decanoyl-2-methoxymethyl glycerol;
1,3-di-undecanoyl-2-methoxymethyl glycerol;
1,3-di-dodecanoyl-2-methoxymethyl glycerol;
1,3-di-tridecanoyl-2-methoxymethyl glycerol;
1,3-di-tetradecanoyl-2-methoxymethyl glycerol;
1,3-di-pentadecanoyl-2-methoxymethyl glycerol;
1,3-di-hexadecanoyl-2-methoxymethyl glycerol;
1,3-di-heptadecanoyl-2-methoxymethyl glycerol;
1,3-di-octadecanoyl-2-methoxymethyl glycerol;
1,3-di-nonadecanoyl-2-methoxymethyl glycerol;
1,3-di-eicosanoyl-2-methoxymethyl glycerol;
1,3-di-p-chlorobenzoyl-2-methoxymethyl glycerol;
1,3-di-o-chlorobenzoyl-2-methoxymethyl glycerol;
1,3-di-m-chlorobenzoyl-2-methoxymethyl glycerol;
1,3-di-p-bromobenzoyl-2-methoxymethyl glycerol;
1,3-di-o-bromobenzoyl-2-methoxymethyl glycerol;
1,3-di-m-bromobenzoyl-2-methoxymethyl glycerol;
1,3-di-p-fluorobenzoyl-2-methoxymethyl glycerol;
1,3-di-o-fluorobenzoyl-2-methoxymethyl glycerol;
1,3-di-m-fluorobenzoyl-2-methoxymethyl glycerol;
1,3-di-p-iodobenzoyl-2-methoxymethyl glycerol;
1,3-di-o-iodobenzoyl-2-methoxymethyl glycerol;
1,3-di-m-iodobenzoyl-2-methoxymethyl glycerol;
1,3-di-toluoyl-2-methoxymethyl glycerol;
1,3-di-phenylacetyl-2-methoxymethyl glycerol;
1,3-di-3-phenylpropanoyl-2-methoxymethyl glycerol;
1,3-di-4-phenylbutanoyl-2-methoxymethyl glycerol.

In a similar manner ethoxymethylacetate, propoxymethylacetate, or butoxymethylacetate can be substituted to prepare the corresponding 1,3-di-acyl-2-alkoxymethyl glycerol.

EXAMPLE 6

1,3-dipivaloyl-2-acetoxymethyl glycerol 50 g of 1,3-dipivaloyl-2-methoxymethyl glycerol, 150 ml of methylene chloride, and 17 ml of acetic anhydride was cooled to about −5° C. Then 0.3 ml of boron trifluoride etherate was added and the mixture was stirred for an additional 1 hr at about 0° C. then allowed to warm to 25° C. over an additional 1.5 hr. After this period, 100 ml saturated aqueous Na₂Cl₃ was added to the mixture followed by 100 ml CH₂Cl₂. After vigorous stirring for 5 min, the organic layer was separated and washed once with 100 ml H₂O, once with aqueous NaCl, dried over anhydrous magnesium sulfate and concentrated in vacuo to afford 1,3-dipivaloyl-2-acetoxymethyl glycerol as a faintly colored oil.

Proton NMR, CDCl₃, 1.2(s, 18H); 2.1(s, 3H); 4.1–4.3(m, 5H); 5.3(s, 2H); 4.7(s, 2H).

Similarly 1,3-di(1-adamantanoyl)-2-acetoxymethyl glycerol, was made.

Proton NMR, CDCl₃, 1.6–2.1(complex, 30H); 2.1(s, 3H); 4.1(complex, 5H); 5.3(s, 2H).
1,3-di-benzoyl-2-acetoxymethyl glycerol;
1,3-di-pivaloyl-2-acetoxymethyl glycerol;
1,3-di-butanoyl-2-acetoxymethyl glycerol;
1,3-di-s-butanoyl-2-acetoxymethyl glycerol;
1,3-di-t-butanoyl-2-acetoxymethyl glycerol;
1,3-di-propanoyl-2-acetoxymethyl glycerol;
1,3-di-hexanoyl-2-acetoxymethyl glycerol;
1,3-di-heptanoyl-2-acetoxymethyl glycerol;
1,3-di-octanoyl-2-acetoxymethyl glycerol;
1,3-di-nonanoyl-2-acetoxymethyl glycerol;
1,3-di-decanoyl-2-acetoxymethyl glycerol;
1,3-di-undecanoyl-2-acetoxymethyl glycerol;
1,3-di-dodecanoyl-2-acetoxymethyl glycerol;
1,3-di-tridecanoyl-2-acetoxymethyl glycerol;
1,3-di-tetradecanoyl-2-acetoxymethyl glycerol;
1,3-di-pentadecanoyl-2-acetoxymethyl glycerol;
1,3-di-hexadecanoyl-2-acetoxymethyl glycerol;
1,3-di-heptadecanoyl-2-acetoxymethyl glycerol;
1,3-di-octadecanoyl-2-acetoxymethyl glycerol;
1,3-di-nonadecanoyl-2-acetoxymethyl glycerol;
1,3-di-eicosanoyl-2-acetoxymethyl glycerol;
1,3-di-p-chlorobenzoyl-2-acetoxymethyl glycerol;
1,3-di-o-chlorobenzoyl-2-acetoxymethyl glycerol;
1,3-di-m-chlorobenzoyl-2-acetoxymethyl glycerol;
1,3-di-p-bromobenzoyl-2-acetoxymethyl glycerol;
1,3-di-o-bromobenzoyl-2-acetoxymethyl glycerol;
1,3-di-m-bromobenzoyl-2-acetoxymethyl glycerol;
1,3-di-p-fluorobenzoyl-2-acetoxymethyl glycerol;
1,3-di-o-fluorobenzoyl-2-acetoxymethyl glycerol;
1,3-di-m-fluorobenzoyl-2-acetoxymethyl glycerol;
1,3-di-p-iodobenzoyl-2-acetoxymethyl glycerol;
1,3-di-o-iodobenzoyl-2-acetoxymethyl glycerol;
1,3-di-m-iodobenzoyl-2-acetoxymethyl glycerol;
1,3-di-toluoyl-2-acetoxymethyl glycerol;

1,3-di-phenylacetyl-2-acetoxymethyl glycerol;
1,3-di-3-phenylpropanoyl-2-acetoxymethyl glycerol;
1,3-di-4-phenylbutanoyl-2-acetoxymethyl glycerol.

In a similar manner ethoxymethylacetate, propoxymethylacetate, or butoxymethylacetate can be substituted to prepare the corresponding 1,3-di-acyl-2-acyloxymethyl glycerol.

EXAMPLE 7
ETHERS AND ESTERS OF DHPG
Dipivaloyl DHPG 8.00 gms of guanine, 40 mls hexamethyldisilazane, 80 mls of xylene and 0.64 gms of ammonium sulfate are refluxed for about 20 hours. 80 ml of volatiles are then distilled out of the resulting clear solution and discarded. 23.1 gms of 1,3-dipivaloyl-2-acetoxymethyl glycerol is then added to the remaining solution and the mixture is refluxed for about 20 hours. After cooling the volatiles are removed in vacuo. The residue is refluxed with 40 mls of isopropanol and then stripped of volatiles in vacuo and then chromatographed over silica gel yielding dipivaloyl DHPG.

Proton NMR, DMSO-$d_6$ 1.1(s, 18H); 3.9–4.3(m, 5H); 5.4(s, 2H); 6.4(s, 2H); 7.8(s, 1H); 10.68(s, 1H).

Similarly 1,3-dibenzyl DHPG

Proton NMR, DMSO-$d_6$ 3.5(m, 4H); 4.1(m, 1H); 4.4(s, 4H); 5.5(s, 2H); 6.7(s, 2H); 7.3(complex, 10H); 7.9(s, 1H); 10.9(s, 1H). was made using 1,3-dibenzyl-2-acetoxymethyl-glycerol as the starting material.

In a similar manner using the appropriate 1,3-dialkyl- or 1,3-diacyl-2-alkanoyloxymethyl glycerol the following ethers and esters of DHPG can be prepared:
9-(1,3-dimethyloxy-2-propoxymethyl)-guanine;
9-(1,3-diethyloxy-2-propoxymethyl)-guanine;
9-(1,3-dipropyloxy-2-propoxymethyl)-guanine;
9-(1,3-diisopropyloxy-2-propoxymethyl)-guanine;
9-(1,3-dibutyloxy-2-propoxymethyl)-guanine;
9-(1,3-di-s-butyloxy-2-propoxymethyl)-guanine;
9-(1,3-di-t-butyloxy-2-propoxymethyl)-guanine;
9-(1,3-diphenyloxy-2-propoxymethyl)-guanine;
9-(1,3-dibenzoyl-2-propoxymethyl)-guanine;
9-(1,3-dibutanoyl-2-propoxymethyl)-guanine;
9-(1,3-di-s-butanoyl-2-propoxymethyl)-guanine;
9-(1,3-di-t-butanoyl-2-propoxymethyl)-guanine;
9-(1,3-di-propanoyl-2-propoxymethyl)-guanine;
9-(1,3-di-hexanoyl-2-propoxymethyl)-guanine;
9-(1,3-di-heptanoyl-2-propoxymethyl)-guanine;
9-(1,3-di-octanoyl-2-propoxymethyl)-guanine;
9-(1,3-di-nonanoyl-2-propoxymethyl)-guanine;
9-(1,3-di-decanoyl-2-propoxymethyl)-guanine;
9-(1,3-di-undecanoyl-2-propoxymethyl)-guanine;
9-(1,3-di-dodecanoyl-2-propoxymethyl)-guanine;
9-(1,3-di-tridecanoyl-2-propoxymethyl)-guanine;
9-(1,3-di-tetradecanoyl-2-propoxymethyl)-guanine;
9-(1,3-di-pentadecanoyl-2-propoxymethyl)-guanine;
9-(1,3-di-hexadecanoyl-2-propoxymethyl)-guanine;
9-(1,3-di-heptadecanoyl-2-propoxymethyl)-guanine;
9-(1,3-di-octadecanoyl-2-propoxymethyl)-guanine;
9-(1,3-di-nonadecanoyl-2-propoxymethyl)-guanine;
9-(1,3-di-eicosanoyl-2-propoxymethyl)-guanine;
9-(1,3-di-p-chlorobenzoyl-2-propoxymethyl)-guanine;
9-(1,3-di-o-chlorobenzoyl-2-propoxymethyl)-guanine;
9-(1,3-di-m-chlorobenzoyl-2-propoxymethyl)-guanine;
9-(1,3-di-p-bromobenzoyl-2-propoxymethyl)-guanine;
9-(1,3-di-o-bromobenzoyl-2-propoxymethyl)-guanine;
9-(1,3-di-m-bromobenzoyl-2-propoxymethyl)-guanine;
9-(1,3-di-p-fluorobenzoyl-2-propoxymethyl)-guanine;
9-(1,3-di-o-fluorobenzoyl-2-propoxymethyl)-guanine;
9-(1,3-di-m-fluorobenzoyl-2-propoxymethyl)-guanine;
9-(1,3-di-p-iodobenzoyl-2-propoxymethyl)-guanine;
9-(1,3-di-o-iodobenzoyl-2-propoxymethyl)-guanine;
9-(1,3-di-m-iodobenzoyl-2-propoxymethyl)-guanine;
9-(1,3-di-toluoyl-2-propoxymethyl)-guanine;
9-(1,3-di-phenylacetyl-2-propoxymethyl)-guanine;
9-(1,3-di-phenylpropanoyl-2-propoxymethyl)-guanine;
9-(1,3-di-phenylbutanoyl-2-propoxymethyl)-guanine.

What is claimed is:

1. A process for preparing a compound represented by the Formula $$R^4-\underset{\underset{O}{\|}}{C}-O-CH_2-O-\begin{bmatrix} O-R^1 \\ O-R^3 \end{bmatrix} \quad \text{Formula A}$$

wherein $R^1$ and $R^3$ are selected from the group consisting of hydrogen, optionally substituted lower alkyl, acyl, optionally substituted phenyl or optionally substituted phenyl lower alkyl and $R^4$ is optionally substituted lower alkyl, comprising:

reacting a compound represented by the Formula $$(R^4-\underset{\underset{O}{\|}}{C}-)_2O \quad \text{Formula B}$$

wherein wherein $R^4$ is independently selected from the group as defined above, with a compound represented by the Formula $$R^6O-CH_2-O-\begin{bmatrix} O-R^1 \\ O-R^3 \end{bmatrix} \quad \text{Formula C'}$$

wherein $R^1$ and $R^3$ are as previously defined, and $R^6$ is defined as optionally substituted lower alkyl, in the presence of a catalyic amount of a Lewis acid for time sufficient to form a compound represented by Formula A.

2. The process of claim 1 wherein the compound represented by Formula C', $R^1$ and $R^3$ are both benzyl.

3. The process of claim 1, wherein $R^4$ is methyl in Formula B.

4. The process of claim 1 wherein said Lewis acid is boron triflouride.

5. The process of claim 1 wherein the compounds represented by Formulas B and C' are reacted for about 60 to 180 minutes at a temperature of between 45° and 65° C.

6. The process of claim 1 wherein the compound represented by Formula C' is a compound wherein $R^1$ and $R^3$ are both (1-adamantanoyl)- and the compound represented by Formula B is acetic anhydride.

7. The process of claim 1 wherein the compound represented by Formula C' is a compound wherein $R^1$ and $R^3$ are both pivaloyl and the compound represented by Formula B is acetic anhydride.

8. A process for preparing the compound of the Formula:

$$R^7-O-CH_2-O-\begin{bmatrix} O-R^1 \\ O-R^3 \end{bmatrix} \quad \text{Formula C}$$

wherein $R^1$ and $R^3$ are selected from the group consisting of hydrogen, optionally substituted lower alkyl, acyl, optionally substituted phenyl or optionally substituted phenyl lower alkyl and $R^7$ is defined as $R^4C(O)OCH_2$ or $R^6OCH_2$ wherein $R^4$ and $R^6$ are defined as optionally substituted lower alkyl, by reacting a compound of Formula D:

$$R^4-\overset{O}{\underset{\|}{C}}-O-CH_2-OR^6 \qquad \text{Formula D}$$

wherein $R^4$ and $R^6$ are as previously defined with a compound of Formula E:

$$R^1-O\diagdown\underset{OH}{\diagup}O-R^3 \qquad \text{Formula E}$$

wherein $R^1$ and $R^3$ are as previously defined, in the presence of a protic acid.

9. The process of claim 8 wherein the protic acid is p-toluene sulfonic acid.

10. The process of claim 8 wherein the reaction mixture is allowed to warm without external heat.

11. A process for preparing a compound represented by Formula A $$R^4-\overset{O}{\underset{\|}{C}}-O-CH_2-O-\underset{\underset{CH_2-O-R^3}{|}}{\overset{CH_2-O-R^1}{|}}CH \qquad \text{Formula A}$$

wherein $R^1$ and $R^3$ are selected from the group consisting of hydrogen, optionally substituted lower alkyl, acyl, optionally substituted phenyl and optionally substituted phenyl lower alkyl; and $R^4$ is optionally substituted lower alkyl;

said process comprising of the steps of:

first, contacting a compound of Formula D $$R^4-\overset{O}{\underset{\|}{C}}-O-CH_2-O-R^6 \qquad \text{Formula D}$$

wherein $R^4$ and $R^6$ are independently selected from optionally substituted lower alkyl,
with a compound of Formula E $$\underset{\underset{CH_2-O-R^3}{|}}{\overset{CH_2-O-R^1}{|}}HO-CH \qquad \text{Formula E}$$

wherein $R^1$ and $R^3$ are defined as above, in the presence of a catalytic amount of a protic acid, to give a mixture of Formula A and a compound represented by Formula C'

$$R^6-O-CH_2-O-\underset{\underset{CH_2-O-R^3}{|}}{\overset{CH_2-O-R^1}{|}}CH \qquad \text{Formula C'}$$

and;

second, contacting said mixture of Formula A and Formula C' with a compound of Formula B $$R^4-\overset{O}{\underset{\|}{C}}-O-\overset{O}{\underset{\|}{C}}-R^4 \qquad \text{Formula B}$$

in the presence of a catalytic amount of a Lewis acid.

12. The process of claim 11 wherein said protic acid is p-toluene sulfonic acid.

13. The process of claim 11 wherein said Lewis acid is boron trifluoride.

14. The process of claim 11 wherein $R^1$ and $R^3$ are both benzyl.

15. The process of claim 11 wherein $R^1$ and $R^3$ are both 1-adamantanoyl.

16. The process of claim 11 wherein $R^1$ and $R^3$ are both pivaloyl.

17. The process of claim 11 wherein the compound represented by Formula B is acetic anhydride.

* * * * *